United States Patent
Pham Duc et al.

(10) Patent No.: US 11,319,264 B2
(45) Date of Patent: May 3, 2022

(54) METHOD FOR PRODUCING A SEPARATION PRODUCT CONTAINING PREDOMINANTLY HYDROCARBONS WITH TWO CARBON ATOMS

(71) Applicant: LINDE AKTIENGESELLSCHAFT, Munich (DE)

(72) Inventors: Tuat Pham Duc, Penzberg (DE); Anne Spindelndreher, Penzberg (DE); Benedikt Kurz, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 525 days.

(21) Appl. No.: 16/325,058

(22) PCT Filed: Aug. 14, 2017

(86) PCT No.: PCT/EP2017/070568
§ 371 (c)(1),
(2) Date: Feb. 12, 2019

(87) PCT Pub. No.: WO2018/029380
PCT Pub. Date: Feb. 15, 2018

(65) Prior Publication Data
US 2021/0284589 A1  Sep. 16, 2021

(30) Foreign Application Priority Data
Aug. 12, 2016 (EP) .................................. 16183935

(51) Int. Cl.
C07C 7/00 (2006.01)
C07C 7/04 (2006.01)
(Continued)

(52) U.S. Cl.
CPC ................ *C07C 7/005* (2013.01); *C07C 7/04* (2013.01); *C07C 7/09* (2013.01); *C07C 7/11* (2013.01);
(Continued)

(58) Field of Classification Search
CPC .. C07C 7/005; C07C 7/04; C07C 7/09; C07C 7/11; C07C 4/08; C07C 4/04; C07C 4/10;
(Continued)

(56) References Cited

U.S. PATENT DOCUMENTS 5,859,304 A * 1/1999 Barchas ................. F25J 3/0252
585/809
2018/0298292 A1* 10/2018 Al-Qahtani ............ F25J 3/0233

FOREIGN PATENT DOCUMENTS

DE   102010014155 A1   10/2011
EP       3029017 A1    6/2016
(Continued)

OTHER PUBLICATIONS

International Search Report for WO2018/029380, dated Nov. 24, 2017, 5 pages.

*Primary Examiner* — Ali Z Fadhel
(74) *Attorney, Agent, or Firm* — Fay Sharpe LLP

(57) ABSTRACT

The invention relates to a method (100) for the recovery of a separation product which contains predominantly hydrocarbons with two carbon atoms, with the use of a separation feedstock which contains predominantly methane, hydrogen and hydrocarbons with two carbon atoms, wherein the methane content of the separation feedstock is up to 20%, and the separation feedstock is provided in a gaseous state. It is provided that, at a first pressure level, the separation feedstock is partially condensed in a single step by cooling from a first temperature level to a second temperature level,
(Continued)

thereby obtaining precisely one first liquid fraction and precisely one first gaseous fraction; at least one part of the first gaseous fraction is partially condensed in a single step through further cooling from the second temperature level to a third temperature level, thereby obtaining precisely one second liquid fraction and precisely one second gaseous fraction; at least one part of the second gaseous fraction at the second pressure level is subjected to a contraflow absorption in the contraflow to an absorption liquid containing predominantly methane, thereby obtaining precisely one third liquid fraction and precisely one third gaseous fraction; the first, the second and the third liquid fraction are at least partially combined and, at least partially, at a second pressure level above the first pressure level, subjected to a low-temperature rectification, thereby obtaining a sump liquid and an overhead gas; at least one part of the overhead gas at the second pressure level is partially condensed in a single step through further cooling from the second temperature level to the third temperature level, thereby obtaining a fourth liquid fraction and a fourth gaseous fraction; and the absorption liquid containing predominantly methane is formed through further cooling of at least a part of the fourth gaseous fraction to a fourth temperature level. A corresponding plant also forms the subject matter of the invention.

13 Claims, 1 Drawing Sheet

(51) Int. Cl.
*C07C 7/09* (2006.01)
*C07C 7/11* (2006.01)
*C10G 5/04* (2006.01)
*C10G 9/00* (2006.01)
*F25J 3/02* (2006.01)
*C07C 4/04* (2006.01)
*C07C 4/08* (2006.01)
*C07C 4/10* (2006.01)

(52) U.S. Cl.
CPC ............... *C10G 5/04* (2013.01); *C10G 9/002* (2013.01); *F25J 3/0219* (2013.01); *F25J 3/0228* (2013.01); *F25J 3/0233* (2013.01); *F25J 3/0238* (2013.01); *C07C 4/04* (2013.01); *C07C 4/08* (2013.01); *C07C 4/10* (2013.01); *C10G 2300/807* (2013.01); *C10G 2400/20* (2013.01)

(58) Field of Classification Search
CPC ........ F25J 3/0238; F25J 3/0228; F25J 3/0233; F25J 3/0219; C10G 5/04; C10G 9/002; C10G 2300/807; C10G 2400/20
See application file for complete search history.

(56) References Cited

FOREIGN PATENT DOCUMENTS

| EP | 3029402 A1 | 6/2016 |
|----|------------|--------|
| WO | 2007045364 A2 | 4/2007 |
| WO | 2015104153 A1 | 7/2015 |
| WO | 2017001514 A1 | 1/2017 |

* cited by examiner

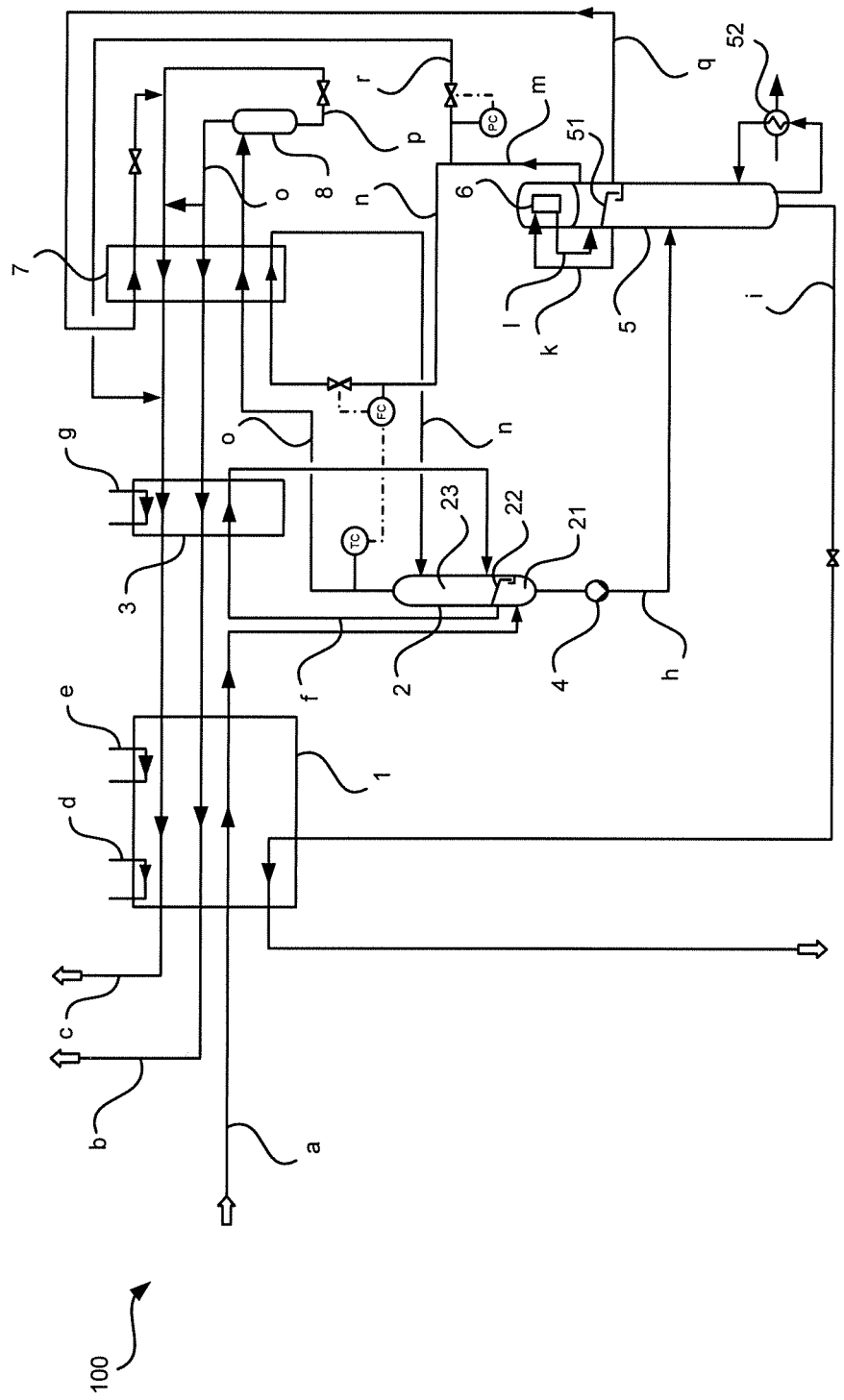

METHOD FOR PRODUCING A SEPARATION PRODUCT CONTAINING PREDOMINANTLY HYDROCARBONS WITH TWO CARBON ATOMS

The invention relates to a method and a plant for the recovery of a separation product containing predominantly hydrocarbons with two carbon atoms according to the preambles of the independent claims.

PRIOR ART

Methods and devices for steam cracking (English: steam cracking) and for the conditioning of the gaseous mixtures obtained in this context are known from the prior art in different embodiments. For further details, reference is made to the relevant specialist literature, for example, the article "Ethylene" in Ullmann's Encyclopedia of Industrial Chemistry, Online edition, 2009, DOI 10.2002/14356007.a10_045.pub3 or Falqi, F.: "The Miracle of Petrochemicals. Olefins Industry: An In-Depth Look at Steam-Crackers", Universal-Publishers 2009, ISBN 1-59942-915-2.

On the commercial scale, steam-cracking methods are implemented in tubular reactors which can, in principle, be charged with a plurality of hydrocarbons and hydrocarbon mixtures from ethane to gas-oil up to a boiling point of typically 600° C. (so-called feedstock). During steam cracking in the tubular reactor or reactors, the feedstock is at least partially converted, thereby obtaining a so-called crude gas. The crude gas can be subjected to a series of post-treatment steps. Such post-treatment steps typically comprise a conditioning of the crude gas by cooling and drying, thereby obtaining a so-called cracked gas. Sometimes, the crude gas is also designated as cracking gas and vice versa.

The cracked gas is a hydrocarbon mixture with hydrocarbons of different chain length and structure. In order to recover the desired products from the cracked gas, the latter must therefore be separated. Different methods are known from the prior art for this purpose and are explained in detail, for example, in the article "Ethylene" in Ullmann's Encyclopedia of Industrial Chemistry, as already mentioned.

In a first separation step, gasoline-like and oil-like components are typically separated if these are present in the cracked gas. For this purpose, oil washes and water washes are typically used. Following this, for example, a gaseous mixture which contains predominantly methane, hydrogen and hydrocarbons with two carbon atoms can initially be separated from the cracked gas. Reference is also made to a "de-ethaniser first"- or "front-end de-ethaniser" method in this context. However, for example, so-called "de-methaniser first"- and "de-propaniser first" methods are also known from the specialist literature.

In order to separate hydrocarbons with two carbon atoms from gaseous mixtures which contain predominantly methane, hydrogen and hydrocarbons with two carbon atoms and which have been formed from the cracked gas of a steam cracking method, separation methods as explained in EP 3 029 017 A1 with reference to FIGS. 1 and 2, can be used. Also WO 2015/104153 A1 discloses a corresponding method. However, such conventional methods are suitable primarily for gaseous mixtures which are formed from a cracked gas which is formed as feedstock in the steam cracking of naphtha and/or heavier hydrocarbons, because, only in this case, is sufficient (at least 30 mole percent) methane contained. Correspondingly high quantities of methane are traditionally required to supply a reflux to the de-methaniser and the C2-absorber (in this regard, see also the explanations for FIG. 1).

Further methods for preparing cracked gases are known from EP 3 029 402 A1, WO 2007/045364 A2, DE 10 2010 014 155 A1 and WO 2017/001514 A1.

However, if mixed feedstocks are used in the steam cracking, that is, if, alongside naphtha, gaseous feedstock such as ethane is also split, the cracked gas and therefore also the gaseous mixture separated from it, containing predominantly methane, hydrogen and hydrocarbons with two carbon atoms, contains comparatively little methane. Accordingly, the de-methaniser and the C2-absorber cannot be operated without further difficulty. In this case, after the separation of hydrogen and the hydrocarbons with two carbon atoms, a part of the methane must be recycled in traditional plants. Methane can be enriched in the circulation through a corresponding recycling. Dependent upon how large the ratio of ethane to naphtha in the feedstock is, the recycling can amount to 15% by weight of the cracked gas. This means that all separation equipment of the crude gas or respectively cracked gas pathway must be designed to be correspondingly larger, and the plant consumes correspondingly more compressor power. Both of these factors are disadvantageous.

One solution proposed in EP 3 029 017 A1 is the external provision of methane. However, in this context, the latter must be constantly available in sufficient quantity and appropriate delivery condition.

In the present case, this raises the object of improving the recovery of separation products containing predominantly hydrocarbons with two carbon atoms from separation feedstocks containing predominantly methane, hydrogen and hydrocarbons with two carbon atoms, such as are formed from cracked gases from steam-cracking methods.

DISCLOSURE OF THE INVENTION

This object is achieved by a method and a plant for the recovery of a separation feedstock containing predominantly hydrocarbons with two carbon atoms with the features of the independent claims. In each case, further developments form the subject matter of the dependent claims and of the subsequent description.

Before explaining the features and advantages of the present invention, their basic principles and the terminology used will be explained.

In the conventional usage here, liquid and gaseous substance mixtures, fractions and similar can be rich or poor in one or more components, wherein "rich" can stand for a content of at least 50%, 75%, 90%, 95%, 99%, 99.5%, 99.9% or 99.99%, and "poor" can stand for a maximum content of 50%, 25%, 10%, 5%, 1%, 0.1% or 0.01% on a molar, weight or volume basis. If reference is made here to the fact that substance mixtures, fractions and similar comprise "predominantly" one or more components, they are "rich" in the latter in the sense explained above. A substance mixture which is "rich" in methane and hydrogen accordingly contains at least 90%, 95%, 99%, 99.5%, 99.9% or 99.99% methane and hydrogen, and other components only in the optionally remaining portion. In the present case, if reference is made, for example, to "methane" or "hydrogen", a fluid should be understood which is rich in the corresponding components, but need not comprise the latter exclusively.

In the conventional usage here, liquid and gaseous substance mixtures can, furthermore, be enriched or depleted in one or more components, wherein these terms relate to a corresponding content in a starting mixture from which the substance mixture was obtained. In the conventional usage here, the substance mixture is "enriched" when it contains at least the 1.1-fold, 1.5-fold, 2-fold, 5-fold, 10-fold, 100-fold or 1000-fold content; by contrast, it is "depleted" when it contains at most the 0.9-fold, 0.5-fold, 0.1-fold, 0.01-fold or 0.001-fold content of a corresponding component, with reference to the starting mixture.

Within the scope of the present invention, rectification and absorption columns are used. Regarding the design and embodiment of corresponding equipment, reference is made to the relevant textbooks (see, for example, K. Sattler: Thermische Trennverfahren [Thermal Separation Methods]. Grundlagen, Auslegung, Apparate [Principles, Design Equipment]. Weinheim: Wiley-VCH, 3rd Edition 2001). Typically, at least one liquid fraction ("some liquid") and one gaseous fraction ("overhead gas") can always be removed from a rectification and an absorption column, from a lower region ("sump") and respectively from an upper region ("head").

In the conventional usage here, a "rectification column" is a separation column which is equipped to separate at least partially a substance mixture presented in gaseous or liquid form or in the form of a two-phase mixture with liquid and gaseous components, optionally also in the super-critical condition, that is, in each case, to generate from the substance mixture pure substances or substance mixtures which are enriched or respectively depleted by comparison with the substance mixture in the sense explained above with regard to at least one component. Typically, rectification columns are constituted as cylindrical metal containers which are fitted with internal structures, for example, sieve trays, ordered or un-ordered packages. A rectification column is characterised, inter alia, in that the sump product is heated by means of a sump evaporator, so that a part is continuously evaporated and rises in gaseous form within the rectification column. Furthermore, a rectification column is typically provided with a so-called overhead condenser, in which at least a part of the overhead gas is liquefied to a condensate and delivered as a liquid reflux at the head of the rectification column. However, a part of the overhead gas can also be used elsewhere, for example, as a product.

By contrast with a rectification column, an "absorption column" typically does not comprise a sump evaporator. In general, absorption columns have long been known in the field of separation technology. Absorption columns are used for absorption in the phase-contraflow and are therefore also designated as contraflow columns. In the case of absorption in the contraflow, the donating gaseous phase flows upwards through an absorption column. The receiving solvent phase, charged from the top and drawn downwards, flows contrary to the gas phase. The gaseous phase is "washed" with the solvent phase. A corresponding absorption column also typically contains internal structures which ensure a step-wise (bottoms, spraying zones, rotating plates etc.) or fixed (random packings of fillers, packings etc.) phase contact. A liquid flow, designated here as the "absorption liquid", is fed into an upper region, by means of which components from a gaseous flow which is fed into a lower region of the absorption column are washed out.

For the characterisation of pressures and temperatures, the present application uses the terms "pressure level" and "temperature level", which is intended to express that corresponding pressures and temperatures need not be used in a corresponding plant in the form of exact pressure or respectively temperature values in order to realise the concept of the invention. However, such pressures and temperatures typically move within given ranges, which are disposed, for example, ±1%, 5%, 10%, 20% or even 50% around a mean value. In this context, corresponding pressure levels and temperature levels can be disposed in separate ranges or in ranges which overlap one another. In particular, for example, pressure levels include unavoidable or anticipated pressure losses, for example, because of cooling effects. The same applies for temperature levels. The pressure levels specified here in bar refer to absolute pressures.

Within the scope of the present invention, ethylene is used, inter alia, at different pressure levels as a cooling agent. The corresponding use of ethylene is known extensively from the prior art. In cooling-agent circulations known from the prior art, ethylene is provided at three pressure levels, a pressure level of approximately 7 to 9 bar ("high-pressure ethylene"), a pressure level of approximately 3 to 4 bar ("medium-pressure ethylene") and a pressure level of approximately 1.15 to 1.4 bar ("low-pressure ethylene"). In this context, a temperature level of approximately −62 to −55° C. can be reached with high-pressure ethylene only; a temperature level of approximately −83 to −76° C. can be reached with medium-pressure ethylene only; and a temperature level of approximately −102 to −98° C. can be reached with low-pressure ethylene only.

Advantages of the Invention

In principle, the method proposed within the scope of the present invention is based on the concepts known from the prior art of recovering separation products containing predominantly hydrocarbons with two carbon atoms from separation feedstocks containing predominantly methane, hydrogen and hydrocarbons with two carbon atoms, which comprise a (partial) condensation, a contraflow absorption and rectification.

Now, however, the present invention is based upon the knowledge that, it is particularly advantageous for the purpose mentioned above, namely the processing of corresponding gaseous mixtures which contain comparatively small quantities of methane, if both a specific, modified cooling of the feedstock and also a given (namely increased by comparison with the cooling) pressure level in the low-temperature rectification, at which the rectification column ("de-methaniser") utilised in a corresponding method is operated, are used. According to one embodiment of the present invention, a modified absorption column is further utilised for the contraflow absorption.

Within the scope of the present invention, the methane content of the separation feedstock is up to 30% (especially on molar basis), and the separation feedstock is presented in gaseous state. The methane content can be, for example, 20 to 25 or 25 to 30 mole percent. Within the scope of the invention, at a first pressure level, the separation feedstock is partially condensed in a single step by cooling from a first temperature level to a second temperature level with the recovery of precisely one first liquid fraction and precisely one first gaseous fraction. Preferred values for the pressure and temperature levels are indicated below.

If a corresponding separation feedstock, is cooled, as in the present invention, not stepwise and with multiple separation of condensates, as explained, for example, in EP 3 029 017 A1, with reference to FIGS. 1 and 2, but in one stage, with only a single separation of one condensate, a larger quantity of methane is transferred into the separated liquid fraction, here, that is, the "first liquid fraction", than in the case of multiple cooling with intermediate separation of the condensates. This is attributable to the fact that, at a higher partial pressure of the methane, the separation feedstock is cooled to the lowest temperature level. In traditional methods, in which larger quantities of methane are available, it is precisely this which is avoided, because methane, which is already separated by the condensation, need no longer be separated in the subsequent separation.

The first liquid fraction is enriched with hydrocarbons with two carbon atoms by comparison with the separation feedstock. However, for the reasons explained, more methane is contained in the first liquid fraction than in the corresponding liquid fractions which are separated in the prior art through a multi-stage partial condensation. By contrast, the first gaseous fraction contains almost the entire hydrogen from the separation feedstock and, by contrast with the latter, is depleted of hydrocarbons with two carbon atoms, but, by contrast, enriched with methane. The further treatment of the first gaseous fraction then serves substantially for the recovery of the hydrocarbons with two carbon atoms.

For this purpose, within the scope of the present invention, at least one part of the first gaseous fraction at the first pressure level is partially condensed in a single step through further cooling to a third temperature level, thereby obtaining precisely one second liquid fraction and precisely one second gaseous fraction. In this manner, a further proportion of the hydrocarbons with two carbon atoms is removed from the first gaseous fraction into the second liquid fraction. However, hydrocarbons with two carbon atoms are still contained in the second gaseous fraction.

Accordingly, at least one part of the second gaseous fraction at the first pressure level is subjected to a contraflow absorption in the contraflow to an absorption liquid containing predominantly methane, thereby obtaining precisely one third liquid fraction and precisely one third gaseous fraction. By means of the absorption liquid containing predominantly methane, the hydrocarbons with two carbon atoms are extensively washed out of the second gaseous fraction. In this manner, a so-called C2-absorber is used.

The first, the second and the third liquid fraction, which contain methane and hydrocarbons with two carbon atoms, are now subjected to a low-temperature rectification which takes place at an increased pressure level. For this purpose, the first, the second and the third liquid fraction are at least partially combined and, at least partially at a second pressure level above the first pressure level, subjected to a low-temperature rectification, thereby obtaining a sump liquid and an overhead gas. Within the scope of the present invention, the increased second pressure level is therefore used in order to ensure that methane can be condensed at the head of the utilised rectification column (the de-methaniser) with low-pressure ethylene, and no colder cooling agents, such as expanding methane, need to be used. In this manner, the reduced quantity of methane in the separation feedstock can be addressed.

Within the scope of the present invention, at least a part of the overhead gas at the second pressure level is partially condensed, especially in a single step, through further cooling to a fourth temperature level, thereby obtaining a fourth liquid fraction and a fourth gaseous fraction, especially precisely one fourth liquid fraction and precisely one fourth gaseous fraction. This typically takes place in an overhead condenser of the rectification column. The fourth temperature level is advantageously achieved in this context with low-pressure ethylene, as explained.

Within the scope of the present invention, the absorption liquid containing predominantly methane is formed through further cooling of at least one part of the fourth gaseous fraction to a fifth temperature level, at which an approximately complete condensation advantageously takes place. The procedure advantageously used in this case is explained below.

Within the scope of the present invention, the first temperature level is at −20 to −35° C., and the second temperature level is at −75 to −80° C., especially at −77 to −79° C. The third temperature level is advantageously at −100 to −105° C., especially at −100 to −102° C., and/or the fourth temperature level is advantageously at −95 to −101° C., especially at −97 to −99° C. The fifth temperature level is advantageously disposed at −140 to −155° C., especially at −148 to −152° C. Furthermore, the first pressure level is advantageously at 32 to 37 bar, especially at 35 to 37 bar, and the second pressure level is advantageously at 35 to 37 bar, and/or the second pressure level is advantageously at 35 to 40 bar, especially at 35 to 37 bar. The advantages of the pressure and temperature levels used specifically within the scope of the present invention have already been explained. Further examples for pressure and temperature levels are explained with reference to FIG. 1.

According to a specially preferred embodiment of the method according to the invention, an absorption column is used for the contraflow absorption, which comprises a sump region and an absorption region separated from the sump region by a liquid barrier, which is arranged above the sump region, wherein the liquid barrier is constituted in such a manner that it allows liquid, which collects in a lower region of the absorption region on the liquid barrier, to drain into the sump region and, in this context, prevents a rising of gas from the sump region upwards into the absorption region. In this manner, the phase separation of the first gaseous fraction from the first liquid fraction, of the second gaseous fraction from the second liquid fraction and the contraflow absorption for the formation of the third gaseous fraction and the third liquid fraction can be implemented in a particularly advantageous manner in a single separation device. The latter can be produced in a particularly economically efficient manner and operated advantageously. In this context, the liquid barrier operates in the manner of a siphon, which allows liquid to drain downwards but no gas to rise upwards. It can be embodied in the manner of a siphon tray known from the field of rectification, wherein, however, a gas passage is dispensed with.

If such a modified absorption column is used, the separation feedstock cooled from the first temperature level to the second temperature level can be fed into the sump region as a two-phase mixture, wherein, within the latter, the first liquid fraction is then separated from the first gaseous fraction. In this context, the liquid fraction need not be present in the form of an independent fraction, but can already be mixed during its formation with the liquid flowing through the liquid barrier from the absorption region.

Furthermore, if a modified absorption column is used, the first gaseous fraction or its part further cooled to the third temperature level can be fed in at the sump end as a two-phase mixture into the absorption region, so that the second liquid fraction is separated there from the second gaseous fraction. Here also, the second liquid fraction need not occur in the form of an independent fraction, but it can be mixed during its formation with charged washing liquid trickling downwards which, as already mentioned, is also designated here as a third liquid fraction. In other words, with the use of a correspondingly modified absorption column, the third liquid fraction can be combined with the second liquid fraction in the case of its formation above the liquid barrier and released via the liquid barrier into the sump region, where it is combined with the first liquid fraction in the case of its formation.

Within the scope of the present invention, the first, the second and the third liquid fraction or its combined parts can advantageously be compressed by means of a sump pump and transferred into a rectification column used for the low-temperature rectification. Since the condensate occurring during the cooling can be brought to pressure, an energy-intensive pressurisation of the entire separation feedstock can be avoided. In fact, a corresponding pump is required, but, for the reasons explained, it is possible to dispense with methane cooling agents or the depressurisation of corresponding flows and a subsequent repressurisation.

Within the scope of the present invention, as already mentioned, it is advantageous if an overhead condenser of the rectification column is used for the partial condensation of the overhead gas or of its part, which is cooled with the use of low-pressure ethylene. Through the increased operating pressure in the rectification column, a condensation with low-pressure ethylene is possible, so that colder cooling agents can be dispensed with.

Within the scope of the present invention, at least a part of the third gaseous fraction at the first pressure level is partially condensed, especially in a single step, by cooling to a fifth temperature level, thereby obtaining a fifth liquid fraction and a fifth gaseous fraction, especially precisely one fifth liquid fraction and precisely one fifth gaseous fraction. In this manner, a separation into a methane-enriched or methane-rich fraction (the fifth liquid fraction) and a hydrogen-enriched or hydrogen-rich fraction (the fifth gaseous fraction) can be achieved. The fractions can be further treated.

It is particularly advantageous in this context if at least one heat exchanger which is cooled with the use of at least one part of the fifth liquid fraction and of the fifth gaseous fraction is used for the cooling of the third and of the fourth gaseous fraction or their parts. In this manner, in each case, temperatures, namely the fifth temperature level, can be achieved for the cooling of the named gaseous fractions, which could not be achieved with the use of low-pressure ethylene.

Within the scope of the present invention, for the cooling of the separation feedstock, at least one heat exchanger is used, which is cooled with the use of at least one part of the fifth liquid fraction and of the fifth gaseous fraction and with high-pressure and medium-pressure ethylene. In this manner, the temperature of the separation feedstock can be adequately reduced, without recourse to excessive quantities of external cooling agent.

By contrast, for the cooling of the first gaseous fraction, at least one heat exchanger is used, which, especially together with at least one part of the fifth liquid fraction and of the fifth gaseous fraction, is cooled with low-pressure ethylene. In this manner, the third temperature level can be achieved.

A plant for the recovery of a separation product which contains predominantly hydrocarbons with two carbon atoms can be used, with the use of a separation feedstock which contains predominantly methane, hydrogen and hydrocarbons with two carbon atoms, wherein the methane content of the separation feedstock is up to 20% and the separation feedstock is provided in the gaseous state.

This plant is characterised by means which are equipped partially to condense the separation feedstock at a first pressure level in a single step by cooling from a first temperature level to a second temperature level, thereby obtaining precisely one first liquid fraction and precisely one first gaseous fraction; partially to condense at least one part of the first gaseous fraction in a single step through further cooling from the second temperature level to a third temperature level, thereby obtaining precisely one second liquid fraction and precisely one second gaseous fraction; to subject at least one part of the second gaseous fraction at the second pressure level to a contraflow absorption in the contraflow to an absorption liquid containing predominantly methane, thereby obtaining precisely one third liquid fraction and precisely one third gaseous fraction; at least partially to combine the first, the second and the third liquid fraction and at least partially to subject the latter at a second pressure level above the first pressure level to a low-temperature rectification, thereby obtaining a sump liquid and an overhead gas; partially to condense in a single step at least one part of the overhead gas at the second pressure level through further cooling to a fourth temperature level, thereby obtaining a fourth liquid fraction and a fourth gaseous fraction; and to form the absorption liquid containing predominantly methane through further cooling of at least a part of the fourth gaseous fraction from the third to a fifth temperature level.

A corresponding plant is advantageously equipped for the implementation of a method as explained previously. At this point, therefore, reference can be made to the named features and advantages.

In the following, the invention is explained in greater detail with reference to the attached drawing, which shows a preferred embodiment of the invention.

BRIEF DESCRIPTION OF THE DRAWINGS

FIG. 1 shows a process according to an embodiment of the invention.

DETAILED DESCRIPTION OF THE DRAWINGS

In FIG. 1, a method according to a particularly preferred embodiment of the invention is illustrated in the form of a schematic process-flow diagram and designated as a whole as 100. The explanations relating to the method 100 apply in a similar manner to a corresponding plant, so that, when reference is made to method steps, the corresponding explanations correspond at the same time to components of the plant and vice versa.

In the method 100, a gaseous mixture containing predominantly methane, hydrogen and hydrocarbons with two carbon atoms which can previously be subjected, for example, to a hydration for the conversion of previously contained acetylene, and which is formed from the cracked gas of a steam cracking method not illustrated here, is provided in gaseous form as a separation feedstock.

The separation feedstock in the form of a substance flow a is cooled in a heat exchanger 1 against a hydrogen fraction (substance flow b), methane fraction (substance flow c), high-pressure ethylene (substance flow d) and medium-pressure ethylene (substance flow e) to a pressure level of approximately 34.9 bar (designated here as "first pressure level"), starting from a temperature level at approximately −23° C. ("first temperature level") to a temperature level of approximately −78° C. ("second temperature level"), in this context, partially condensed in a single step and then guided at a pressure level of approximately 34.7 bar (accordingly, still the first pressure level) into the sump region 21 of an absorption column 2 of the C2 absorber. There, the condensate occurring ("first liquid fraction") is separated from the gaseous phase f ("first gaseous fraction").

The first liquid fraction is enriched with hydrocarbons with two carbon atoms. Because of the single-stage partial condensation, a comparatively large quantity of methane is separated from the separation feedstock in the first liquid fraction. This is larger than it would be in a conventional multi-stage partial condensation, as illustrated, for example, in EP 3 029 017 A1 with reference to FIGS. 1 and 2. The first gaseous fraction contains substantially all the components of the separation feedstock, but is, in particular, depleted with regard to hydrocarbons with two carbon atoms. By comparison with conventional multi-stage partial condensations, it also contains less methane for the reasons mentioned.

In the illustrated example, the first gaseous fraction is withdrawn completely from the sump region 21 of the absorption column 2 in the form of a substance flow f and further cooled in a heat exchanger 3 against the already mentioned hydrogen and methane fraction (substance flows b and c) and against low-pressure ethylene (substance flow g), to a temperature level of approximately −103° C. ("third temperature level") and, in turn, partially condensed. Because of the use of the substance flows b and c, the third temperature level is lower than would be attainable with low-pressure ethylene alone. After this, the substance flow f is recycled, still as a two-phase mixture, back into the absorption column 2 above a liquid barrier 22, which divides the sump region 21 of the absorption column 2 from an absorption region 23 disposed above it. The liquid barrier 22 allows a downward flow of liquid accumulating in the lower region of the absorption region 23 and prevents a rising upwards of gas from the sump region 21 into the absorption region 23.

In order to overcome the pressure loss in the heat exchanger 3, the latter is arranged geodetically above the absorption column 2. The absorption column 2 operates at a pressure level of approximately 34 to 35 bar, that is, also at the first pressure level already mentioned several times.

In the absorption column 2 or respectively its absorption region, a phase separation of the substance flow f or respectively of the correspondingly cooled first gaseous fraction, takes place. The liquid phase ("second liquid fraction") accumulates above the liquid barrier 22 and is combined there with charged absorption liquid ("third liquid fraction") trickling downwards from above. The gaseous proportion ("second liquid fraction") remaining in the case of the phase separation of the substance flow f or respectively of the correspondingly cooled first gaseous fraction rises upwards into the absorption region and, in this context, is subjected to a contraflow absorption in the contraflow to an absorption liquid containing predominantly methane, in the form of a substance flow n.

In the contraflow absorption, a liquid fraction (the "third liquid fraction" already mentioned) is formed, which combines with the second liquid fraction, as already mentioned. The second and third liquid fraction drain in combination via the liquid barrier 22 into the sump region 21 of the absorption column 2, where they are combined with the first liquid fraction. The gaseous fraction remaining ("third gaseous fraction") in the case of the contraflow absorption rises upwards and is withdrawn from the absorption column 2 in the form of a substance flow o.

From the sump region 21 of the absorption column 2, the combined first, second and third liquid fraction is withdrawn by means of a sump pump 4 at a temperature of approximately −79° C. (that is, still at the first temperature level) from the absorption column 2, more precisely from the sump region 21, and pumped (substance flow h) into a rectification column 5, the so-called de-methaniser. Through the action of the sump pump 4, a pressurisation to approximately 38 bar occurs. In the rectification column 5, the hydrocarbons with two carbon atoms, that is, the "separation product" mentioned several times, at a pressure level of approximately 35 bar ("second pressure level") are separated from methane and lighter components and leave the rectification column 5 via the sump as sump liquid in the form of a substance flow i. In general, the rectification column 5 operates at the second pressure level, especially at approximately 35 to 36 bar, its sump is evaporated off in a sump evaporator 52 with high-pressure propylene. The substance flow i, that is, the separation product, can be warmed in the heat exchanger 1 and supplied to a further separation step for the separation of hydrocarbons with two carbon atoms from one another.

Overhead gas of the rectification column 5 is cooled in the form of a substance flow k in a heat exchanger 6 with the use of low-pressure ethylene, which is present at a temperature level of approximately −101° C., to a temperature level of approximately −98° C. ("fourth temperature level") and partially condensed. The heat exchanger 6 is built into the head of the rectification column 5, so that the occurring condensate ("fourth liquid fraction") flows back into the rectification column 5 as a reflux in the form of a substance flow l, without a pump only through gravity. Because here, only low-pressure ethylene is used, the fourth temperature level is disposed above the third temperature level which is provided by the heat exchanger 3. The remaining gas ("fourth gaseous fraction") comprises predominantly methane and leaves the rectification column 5 at the head in the form of a substance flow m. The majority of this substance flow m is further cooled in the form of a substance flow n in a heat exchanger 7 to a temperature level of approximately −152° C. ("fifth temperature level"), during this course, predominantly condensed, and then, as already mentioned, supplied as reflux to the absorption region 23 of the absorption column 2.

The overhead product of the absorption region 23 of the absorption column 2 (that is, the third gaseous fraction) is also cooled in the form of a substance flow o, which is present at a pressure level of approximately 34.4 bar (that is, the first pressure level), in the heat exchanger 7 to the fifth temperature level of approximately −152° C. and partially condensed. In a separation container 8, the condensate occurring, the so-called methane fraction ("fifth liquid fraction"), is separated from the gaseous phase, the so-called hydrogen fraction ("fifth gaseous fraction"). The methane fraction, here initially still designated with p, is first depressurised to an appropriate pressure level, for example, of a heating gas network, and then warmed in the heat exchangers 7, 3 and 1.

For the cold-balancing of the heat exchanger 7, liquid methane is removed from the rectification column 5 above a liquid tray 51 and supplied in the form of a substance flow q to the methane fraction of the substance flow p, after it has been cooled in the heat exchanger 7 to the fifth temperature level of approximately −152° C. Similarly, a small part of the substance flow m can be fed in the form of a substance flow r to the substance flow p. The combined flow formed from the substance flows p, q and r is still designated as a methane fraction and is illustrated in the form of the already mentioned substance flow c.

The gaseous phase with approximately 90 mole percent hydrogen from the separation container 8, is warmed, like the methane fraction of the substance flows p and respectively c, in the heat exchangers 7, 3 and 1, against the warm substance flow a.

The invention claimed is:

1. A method for the recovery of a separation product which contains predominantly hydrocarbons with two carbon atoms comprising:
providing a separation feedstock which contains predominantly methane, hydrogen and hydrocarbons with two carbon atoms, wherein the methane content of the separation feedstock is up to 30%, and the separation feedstock is provided in a gaseous state,
partially condensing the separation feedstock at a first pressure level in a single step by cooling from a first temperature level at −20 to −35° C. to a second temperature level at −75 to −80° C., and recovering one first liquid fraction and one first gaseous fraction
partially condensing at least a part of the first gaseous fraction at the first pressure level in a single step through further cooling to a third temperature level, thereby obtaining one second liquid fraction and one second gaseous fraction,
subjecting at least one part of the second gaseous fraction at the first pressure level to a contraflow absorption with an absorption liquid containing predominantly methane, thereby obtaining one third liquid fraction and one third gaseous fraction,
combining, at least partially, the first, the second and the third liquid fraction and, at a second pressure level above the first pressure level, at least partially subjecting the combined liquid fractions to a low-temperature rectification, thereby obtaining a sump liquid and an overhead gas,
partially condensing at least a part of the overhead gas at the second pressure level in a single step through further cooling to a fourth temperature level, thereby obtaining a fourth liquid fraction and a fourth gaseous fraction,
cooling at least a part of the fourth gaseous fraction to a fifth temperature level to form at least a portion of the absorption liquid containing predominantly methane.

2. The method according to claim 1, in which the third temperature level is at −100 to −105° C., and/or the fourth temperature level is at −95 to −100° C., and/or the fifth temperature level is at −140 to −155° C.

3. The method according to claim 1, in which the first pressure level is at 32 to 37 bar, and/or the second pressure level is at 35 to 40 bar.

4. The method according to claim 1, in which, for the contraflow absorption, an absorption column is used, which comprises a sump region and an absorption region separated from the sump region by a liquid barrier, which is arranged above the sump region, wherein the liquid barrier is constituted in such a manner that it allows liquid which collects in a lower region of the absorption region on the liquid barrier, to drain downwards into the sump region and, in this context, prevents a rising upwards of gas from the sump region into the absorption region.

5. The method according to claim 4, in which the separation feedstock cooled from the first temperature level to the second temperature level is fed into the sump region as a two-phase mixture, wherein, within the latter, the first liquid fraction is separated from the first gaseous fraction.

6. The method according to claim 5, in which the first gaseous fraction or its part further cooled to the third temperature level is fed at the sump end as a two-phase mixture into the absorption region, wherein, within the latter, the second liquid fraction is separated from the second gaseous fraction.

7. The method according to claim 6, in which the third liquid fraction is combined with the second liquid fraction, the liquid barrier and released via the liquid barrier into the sump region, where it is combined with the first liquid fraction.

8. The method according to claim 1, in which the first, the second and the third liquid fraction or their combined parts are compressed by means of a sump pump and transferred into a rectification column used for the low-temperature rectification.

9. The method according to claim 8, in which, for the partial condensation of the overhead gas or of its part, an overhead condenser of the rectification column which is cooled with the use of low-pressure ethylene is used.

10. The method according to claim 1, in which at least a part of the third gaseous fraction at the first pressure level is partially condensed in a single step through further cooling to the fifth temperature level, thereby obtaining precisely one fifth liquid fraction and precisely one fifth gaseous fraction.

11. The method according to claim 10, in which, for the cooling of the third and of the fourth gaseous fraction or their parts, at least one heat exchanger is used, which is cooled with the use of at least one part of the fifth liquid fraction and the fifth gaseous fraction.

12. The method according to claim 10, in which, for the cooling of the separation feedstock, at least one heat exchanger is used, which is cooled with the use of at least one part of the fifth liquid fraction and of the fifth gaseous fraction and with high-pressure and medium-pressure ethylene.

13. The method according to claim 1, in which, for the cooling of the first gaseous fraction, at least one heat exchanger is used, which is cooled with the use of at least one part of the fifth liquid fraction and of the fifth gaseous fraction and with low-pressure ethylene.

* * * * *